(12) United States Patent
Heck

(10) Patent No.: US 10,076,626 B2
(45) Date of Patent: Sep. 18, 2018

(54) SYSTEM AND METHODS FOR RESPIRATORY SUPPORT USING LIMITED-LEAK CANNULAS

(71) Applicant: Louis John Heck, St. Cloud, MN (US)

(72) Inventor: Louis John Heck, St. Cloud, MN (US)

( * ) Notice: Subject to any disclaimer, the term of this patent is extended or adjusted under 35 U.S.C. 154(b) by 675 days.

(21) Appl. No.: 14/505,214

(22) Filed: Oct. 2, 2014

(65) Prior Publication Data
US 2015/0174357 A1 Jun. 25, 2015

Related U.S. Application Data

(60) Provisional application No. 61/885,818, filed on Oct. 2, 2013.

(51) Int. Cl.
*A61M 16/00* (2006.01)
*A61M 16/06* (2006.01)
(Continued)

(52) U.S. Cl.
CPC .... *A61M 16/0666* (2013.01); *A61M 16/0003* (2014.02); *A61M 16/0051* (2013.01);
(Continued)

(58) Field of Classification Search
CPC .......... A61M 16/0666; A61M 16/0003; A61M 16/0069; A61M 16/202; A61M 16/0672;
(Continued)

(56) References Cited

U.S. PATENT DOCUMENTS 5,094,246 A * 3/1992 Rusz .................... A61B 5/0816
128/205.23
D434,496 S 11/2000 Choksi et al.
(Continued)

FOREIGN PATENT DOCUMENTS

WO 2015051143 4/2015

OTHER PUBLICATIONS

Ahluwalia, Jag et al., "Draeger Volume Guarantee," New Approaches in Volume Controlled Ventilation for Neonates, 2010 (68 pages).
(Continued)

*Primary Examiner* — Steven Douglas
(74) *Attorney, Agent, or Firm* — Pauly, DeVries Smith & Deffner LLC

(57) ABSTRACT

Various embodiments include systems and methods related to respiratory support delivered to infants using limited-leak cannulas. Various embodiments include a method of providing respiratory support to an infant. The method can include attaching a limited-leak cannula having prongs to an inspiratory port of a ventilator with connection tubing. The method can include selecting an operations mode on the ventilator that is specific for unidirectional flow limited-leak cannula use. The method can include initiating a calibration procedure with the prongs of the cannula freely exposed. The calibration procedure can include measuring the flow rate of gas through the connection tubing at a set pressure. The method can include setting monitoring parameters on the ventilator, initiating respiratory support by inserting the cannula prongs into the nares of the infant, and continuously monitoring the flow rate of gas through the limited-leak cannula. Other embodiments are also included herein.

17 Claims, 4 Drawing Sheets

(51) Int. Cl.
*A61M 16/20* (2006.01)
*A61M 16/08* (2006.01)
*A61B 5/087* (2006.01)

(52) U.S. Cl.
CPC ...... *A61M 16/0069* (2014.02); *A61M 16/026* (2017.08); *A61M 16/0672* (2014.02); *A61M 16/202* (2014.02); *A61B 5/0878* (2013.01); *A61B 2503/045* (2013.01); *A61M 16/0683* (2013.01); *A61M 16/0816* (2013.01); *A61M 2016/003* (2013.01); *A61M 2016/0027* (2013.01); *A61M 2016/0039* (2013.01); *A61M 2205/15* (2013.01); *A61M 2205/3303* (2013.01); *A61M 2205/3334* (2013.01); *A61M 2205/3344* (2013.01); *A61M 2205/502* (2013.01); *A61M 2205/52* (2013.01); *A61M 2205/70* (2013.01); *A61M 2230/46* (2013.01); *A61M 2240/00* (2013.01)

(58) Field of Classification Search
CPC .......... A61M 16/0051; A61M 2230/46; A61M 2205/502; A61M 2205/3344; A61M 2205/15; A61M 2205/3334; A61M 2016/003; A61M 2205/70; A61M 2205/3303; A61M 2205/52; A61M 16/0683; A61M 2016/0039; A61M 16/0816; A61M 2016/0027; A61M 2240/00; A61B 5/0878; A61B 2503/045
See application file for complete search history.

(56) References Cited

U.S. PATENT DOCUMENTS

| | | |
|---|---|---|
| D439,973 S | 4/2001 | Choksi |
| D506,547 S | 6/2005 | Cruz et al. |
| 7,635,361 B2 | 12/2009 | Mccrary et al. |
| 8,001,966 B1 | 8/2011 | Goldstein et al. |
| 8,267,083 B1 | 9/2012 | Goldstein et al. |
| 8,353,296 B1 | 1/2013 | Heyman et al. |
| D681,193 S | 4/2013 | Thornbury et al. |
| 2002/0078958 A1 | 6/2002 | Stenzler |
| 2004/0074495 A1* | 4/2004 | Wickham ............ A61M 16/00 128/204.18 |
| 2009/0149730 A1 | 6/2009 | Mccrary et al. |
| 2009/0253995 A1* | 10/2009 | Lewis .................... A61B 5/087 600/538 |
| 2010/0218767 A1 | 9/2010 | Jafari et al. |
| 2010/0236555 A1 | 9/2010 | Jafari et al. |
| 2012/0318266 A1 | 12/2012 | Chou |

OTHER PUBLICATIONS

"Babylog VN500 Ventilation Unit SW 2.n," Instructions for Use Infinity Acute Care System, Draeger Medical AG & Co. KG, Jun. 2009, (284 pages).

"International Preliminary Report on Patentability," for PCT/US2014/058861 dated Feb. 26, 2015, 12 pages.

"Neotech RAM Cannula," Suggested Settings, Directions for Use and Frequently Asked Questions, Neotech Products, Inc., (2 pages).

"Workstation Neonatal Care—Draeger Babylog VN500," Technical Data, Draegerwerk AG & Co. KG, 2010 (4 pages).

"International Preliminary Report on Patentability," for PCT Application No. PCT/US2014/058861, dated Apr. 14, 2016 (8 pages).

* cited by examiner

SYSTEM AND METHODS FOR RESPIRATORY SUPPORT USING LIMITED-LEAK CANNULAS

This application claims the benefit of U.S. Provisional Application No. 61/885,818, filed Oct. 2, 2013, the content of which is herein incorporated by reference in its entirety.

FIELD OF THE INVENTION

The present invention relates to respiratory support using limited-leak cannulas (LLC). More specifically, the present invention relates to systems and methods regarding respiratory support delivered to infants using limited-leak cannulas.

BACKGROUND OF THE INVENTION

Newborn infants, both preterm and term, may experience respiratory distress as a result of various conditions including respiratory distress syndrome of the newborn (a.k.a. hyaline membrane disease), wet lung syndrome of the newborn, intrauterine pneumonia, postnatal pneumonia, meconium aspiration syndrome, persistent pulmonary hypertension of the newborn (a.k.a. persistent fetal circulation), pulmonary hypoplasia, and certain neurological conditions. Some newborn infants with respiratory distress are judged to require treatment with different types of respiratory support.

In the context of systems for delivering respiratory support, nasal cannulas are devices that deliver gases directly to the nares of a patient. There are two primary types of nasal cannulas: standard nasal cannulas and limited-leak cannulas. Standard nasal cannulas are used to deliver gases into the nares at a fixed flow rate. In contrast, limited-leak cannulas are used by setting a pressure level or levels rather than flow rate(s). In order to function properly, the prongs of a limited-leak cannula, though larger than those of a standard cannula, cannot form a seal with the nares, but rather a leak is required at the nasal level allowing continuous unidirectional flow. An example of a limited-leak cannula is the RAM Cannula commercially available from Neotech Products, Inc., Valencia, Calif.

SUMMARY OF THE INVENTION

Embodiments of the invention include systems and methods related to respiratory support delivered to infants using limited-leak cannulas. In an embodiment, the invention includes a method of providing respiratory support to an infant. The method can include attaching a limited-leak cannula having prongs to an inspiratory port of a ventilator with connection tubing. The method can include entering specific patient data, such as operational weight. The method can include selecting an operations mode on the ventilator that is specific for unidirectional flow limited-leak cannula use. The method can include initiating a calibration procedure with the prongs of the cannula freely exposed. The calibration procedure can include measuring the flow rate of gas through the connection tubing at a set pressure. The method can include setting monitoring parameters on the ventilator. The monitoring parameters can include bounds of a range for desired flow rate. The method can include initiating respiratory support by inserting the cannula prongs into the nares of the infant. The method can further include continuously monitoring the flow rate of gas and flow rate pattern through the limited-leak cannula while positioned in the nares of the patient. The method can further include observing the flow rate pattern during spontaneous breathing for a decreased difference in flow rate between inspiration and expiration below a predetermined threshold as evidence of possible nasal airway obstruction.

In an embodiment, the invention includes a method of controlling ventilator operations. The method can include receiving user input of specific patient data, such as operational weight. The method can include receiving instructions from a system user to initiate an operations mode specific for limit-leak cannulas. The method can include executing a calibration procedure. The calibration procedure can include measuring the gas flow rate at a set pressure from a gas source. The ventilator can be connected to a limited-leak cannula having prongs during the calibration procedure with the prongs freely exposed to ambient air pressure. The gas flow rate can be measured using a flow sensor in a conduit in fluid communication with an inspiratory gas port of the ventilator and the limited-leak cannula. The method can further include equating the measured flow rate at the set pressure with a 100% leak condition for purposes of calculating leak percentage. The method can further include monitoring the measured flow rate and flow rate pattern after the prongs of the limited-leak cannula are inserted into the nares of an infant. The method can further include processing the measured flow rate to correct for artifactual changes to determine an effective current flow rate. The method can further include monitoring the effective current flow rate to detect flow rates that deviate from a predetermined target flow rate range and issuing a system warning if the effective current flow rate deviates from the predetermined target flow rate range. The method can further include monitoring the flow rate pattern during spontaneous breathing for a decreased difference in flow rate between inspiration and expiration below a predetermined threshold, and notifying the user of the change as evidence of possible nasal airway obstruction.

In an embodiment, the invention includes a medical ventilator including a control unit with a microprocessor and a memory, a control interface in electrical communication with the control unit, a gas supply, a control valve in fluid communication with the gas supply, the control unit configured to adjust the control valve, and an inspiratory gas orifice in fluid communication with the control valve. The system can include a pressure sensor in fluid communication with the inspiratory gas orifice and a flow sensor in fluid communication with the inspiratory gas orifice. The control unit can be configured to receive instructions from the system user through the control interface regarding entering a mode of operation specific to delivering respiratory support to a patient using a limited-leak cannula. The mode of operation specific to delivering respiratory support can include execution of a calibration operation including measuring the flow rate of gas through a conduit in fluid communication with the inspiratory gas orifice while a limited-leak cannula is operatively connected to the inspiratory gas orifice and prongs of the limited-leak cannula are freely exposed to ambient gas pressure. The mode of operation specific to delivering respiratory support can further include monitoring the measured flow rate after the prongs of the limited-leak cannula are inserted into the nares of an infant and processing the measured flow rate to correct for artifactual changes to determine an effective current flow rate. The mode of operation specific to delivering respiratory support can further include monitoring the effective current flow rate to detect flow rates that deviate from a predetermined target flow rate range and issuing a system warning if the effective current flow rate deviates from the predetermined target flow rate range. The mode of operation specific to delivering respiratory support can further include monitoring the flow rate pattern during spontaneous breathing for a decreased difference in flow rate between inspiration and expiration below a predetermined threshold, and notifying the user of the change as evidence of possible nasal airway obstruction.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

While the invention may encompass various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and operations of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As described above, a limited-leak cannula requires continuous unidirectional flow and a leak at the nasal level in order to function properly. However, existing ventilators equate unidirectional flow with a large leak (a typical alarm condition for such ventilators) thus presenting an obstacle to using limited-leak cannulas in conjunction with the sophisticated flow monitoring equipment associated with various ventilators. In specific, this results in lack of an intrinsic means of detecting dislodgement or obstruction, lack of information regarding flow rate through the limited-leak cannula, and reliance on conventional infant monitor alarms for abnormal hemoglobin-oxygen saturation, heart rate, or respiratory rate, for notification of dislodgement or obstruction. Embodiments herein can provide solutions to these limitations of using limited-leak cannulas with ventilators.

Figure 1:
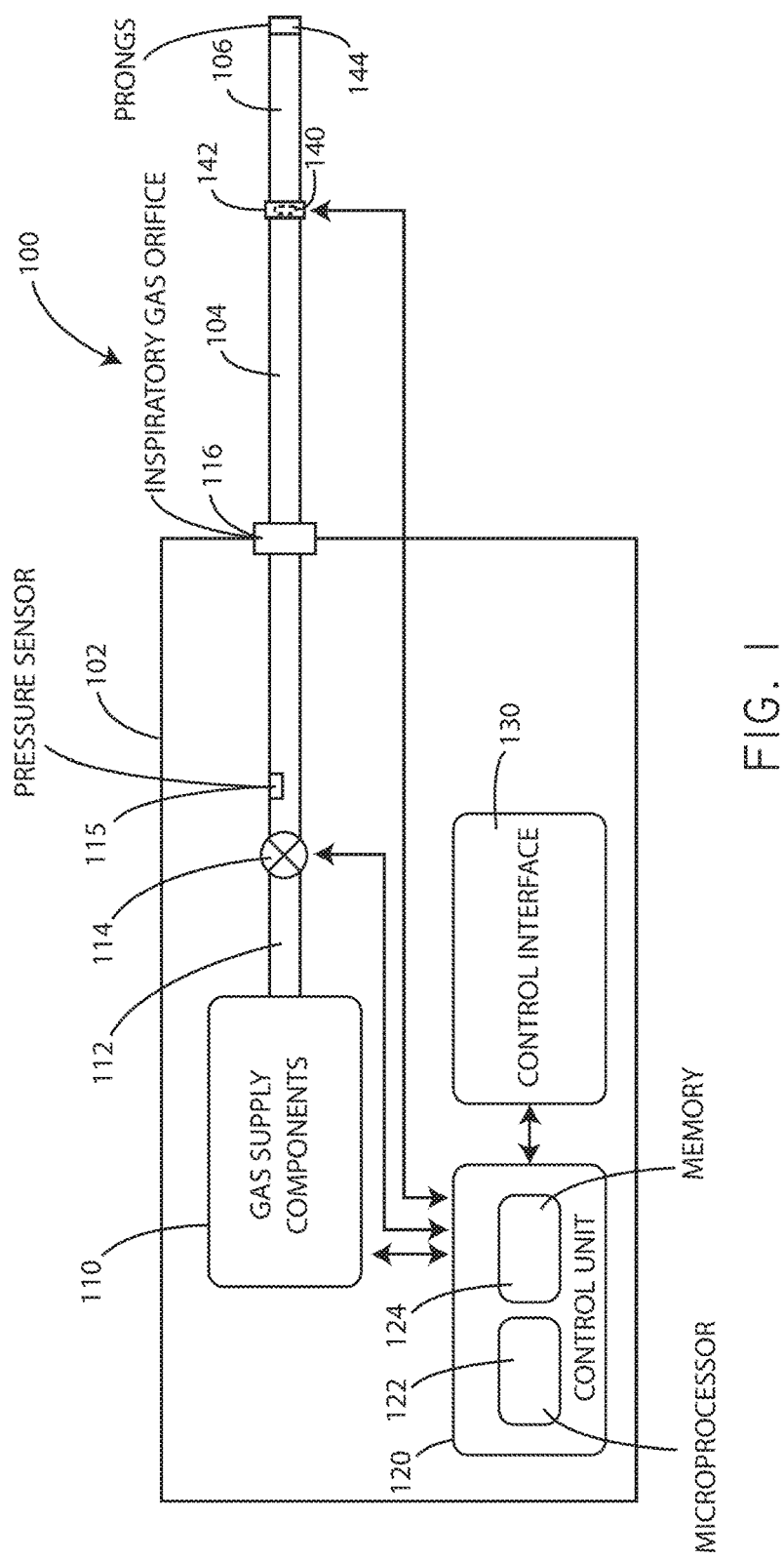
FIG. 1 is a schematic view of a system for providing respiratory support to an infant in accordance with various embodiments herein.

Referring now to FIG. 1, a schematic view of a system 100 for providing respiratory support to an infant in accordance with various embodiments herein. The system 100 can include a ventilator 102, a connection tubing 104, and a limited-leak cannula 106.

The ventilator 102 can include gas supply components 110, a gas flow channel 112, a control valve 114, a pressure sensor 115, an inspiratory gas orifice 116, a control unit 120, and a control interface 130. The gas supply components 110 can include, but are not limited to, gas supply tanks (including but not limited to tanks of substantially pure gases such as an $O_2$ as well as mixed gases), gas input orifices, meters, various sensors (including but not limited to flow sensors, pressure sensors, $O_2$ sensors, and the like), valves, and the like. The gas flow channel 112 can facilitate the movement of gas within the ventilator 102. In some embodiments, gas can pass through a control valve 114 as it passes through the gas flow channel 112. The control valve 114 can serve to regulate the flow of gas and can be manipulated via the control unit 120. In various embodiments, the ventilator 102 can include a pressure sensor 115. The ventilator 102 can also include an inspiratory gas orifice 116. The inspiratory gas orifice 116 can serve as the point where gas to be delivered to the patient for inspiration leaves the ventilator 102. The inspiratory gas orifice 116 can serve as a point to connect a device such as connecting tubing 104 in order to convey the gas to the patient. While not shown herein, it will be appreciated that various embodiments can also include an expiratory gas orifice and associated components to handle expiratory gas.

In some embodiments, a flow sensor 140 can be disposed in fluid communication with the gas supply to the limited-leak cannula 106. In some embodiments, a flow sensor 140 can be disposed on or within the connecting tubing 104. The connecting tubing 104 can interface with a limited-leak cannula 106 at a junction 142. The limited-leak cannula 106 can include prongs 144.

It will be appreciated that the flow sensor 140 can be of various types. In some embodiments, the flow sensor can specifically include a hot wire anemometer. Other types of flow sensors can include, but are not limited to, turbine flow sensors, vortex flow sensors, gear flow sensors, thermal mass flow sensors, variable area flow sensors, orifice flow sensors, and the like.

The control unit 120 can include various components. The control unit 120 can be configured to cause the execution of various operations described in greater detail below. The control unit 120 can include a microprocessor 122, or similar device or processor. The control unit 120 can also include memory 124 (which can include various types of volatile or non-volatile memory). It will be appreciated that the control unit 120 can include various other electronic components including, but not limited to, a battery, timer circuits, various input/output channels, a data bus, registers, and the like.

The control unit 120 can be in communication with a control interface 130. The control interface 130 can be configured to handle system inputs and outputs with regard to system users. The control interface 130 can include components to facilitate accepting user input through various devices such as a keyboard, mouse, touchscreen, microphone and the like. The control interface 130 can also include components to facilitate output such as a display screen, touchscreen, speaker, and the like.

Various data can be displayed to the system user through the control interface 130. By way of example, one or more of the following can be displayed: linear display of ventilator pressure vs. time; linear display of LLC flow rate vs. time during spontaneous breathing; linear display of flow rate vs. time during nasal intermittent mandatory ventilation (NIMV); linear display of flow rate vs. time during nasal synchronized intermittent mandatory ventilation (NSIMV); two dimensional pressure vs. flow rate loops for NIMV and NSIMV.

Figure 2:
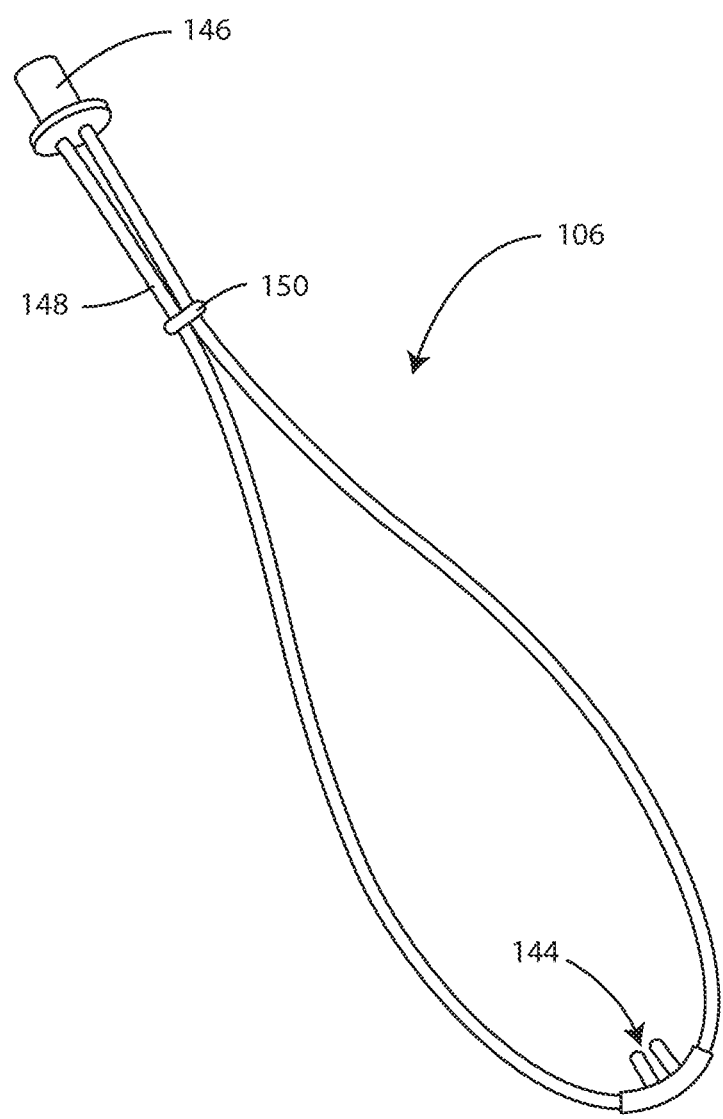
FIG. 2 is a schematic view of a limited-leak cannula used for providing respiratory support to an infant in accordance with various embodiments herein.

Referring now to FIG. 2, a schematic view of a limited-leak cannula 106 used for providing respiratory support to an infant is shown in accordance with various embodiments herein. The limited-leak cannula 106 can include a standard adapter 146, or similar connecting fixture such as connector fitting, a length of tubing 148, prongs 144 for nasal interface, and, optionally, a moveable binder 150 to aid in securing the limited-leak cannula 106 with regard to the patient.

Standard nasal cannulas are used to provide flow of gas into the nares at a fixed flow rate to deliver an increased concentration of oxygen, nasal washout of carbon dioxide and perhaps production of some level of nasal continuous positive airway pressure (NCPAP), though the pressure level is unpredictable and highly variable with attendant risks. In contrast, respiratory support using the limited-leak cannula in the embodiments herein is provided by a fixed pressure setting or fixed pressure settings, and is thereby capable of providing a consistent, predictable and therefore safer level of nasal continuous positive airway pressure (NCPAP), or nasal ventilation, due to a primary characteristic that distinguishes it from standard nasal cannulas, i.e. larger size of the prongs 144 proportionately fitted to an infant's nares to allow a continuous, but limited, leak of gas around the prongs. To function properly in the embodiments described herein, the limited-leak cannula requires continuous unidirectional flow without forming a seal with the nares. The optimal prong size allows a leak from the infant's nares around the prongs, but at a rate less than the maximum flow rate through the cannula at any given pressure setting at the control interface FIG. 1, 130, thereby allowing continuous positive pressure to accumulate in the nasal airway, limited by the pressure setting. When the nasal airway pressure at the exit from the prongs equilibrates with the set pressure, the flow rate through the limited-leak cannula decreases to a rate equal to the flow rate out the nares.

Methods

Figure 3:
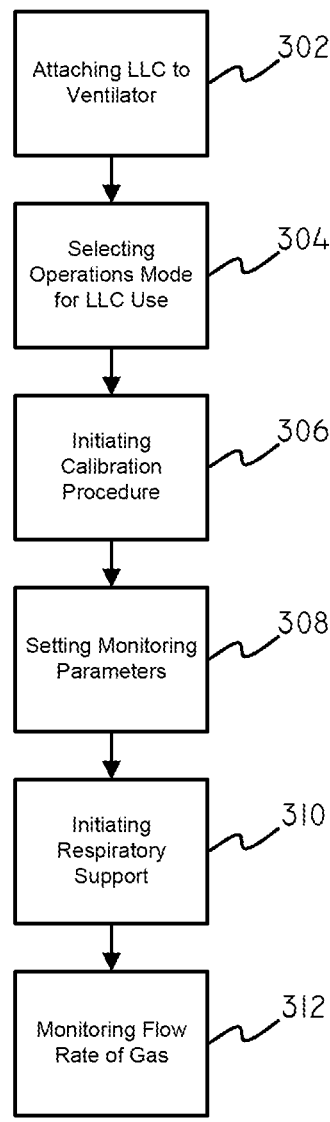
FIG. 3 is a flow chart of operations in accordance with various embodiments herein.

It will be appreciated that systems herein can be configured to execute various operations and/or methods. Referring now to FIG. 3, a flow chart of operations in accordance with various embodiments herein is shown. In an embodiment, the method can be a method of providing respiratory support to an infant. The method can include an operation of attaching 302 a limited-leak cannula having prongs to an inspiratory port of a ventilator with a connection tubing. The method can further include an operation of selecting 304 an operations mode on the ventilator that is specific for unidirectional flow limited-leak cannula use. The method can further include initiating 306 a calibration procedure with the prongs of the cannula freely exposed. In some embodiments, the calibration procedure can include measuring the flow rate of gas through the connection tubing at a set pressure. In some embodiments, the flow rate can be measured with a hot wire anemometer. However, it will be appreciated that flow rate can also be measured via many other types of flow sensors such as those listed above.

The method can further include an operation of setting 308 monitoring parameters on the ventilator. The monitoring parameters can include the bounds (or limits) of a range for desired flow rate. For example, a user can input an upper limit of the desired flow rate range and a lower limit of the desired flow rate range. If the upper limit is exceeded, this can be indicative of the limited-leak cannula becoming dislodged. If the flow rate decreases below the lower limit, this can be indicative of a blockage of the nasal prongs or disruption in the supply of gas. The limits can be specified by the user in various ways. For example, the limits can be specified as absolute differences in flow rate above zero and below the maximum flow rate, or as percentages of the maximum flow rate above zero and below the maximum flow rate. The monitoring parameters can also include duration thresholds such that the measured flow rate must be out of the specified range for a certain period of time before an alarm condition results.

The method can further include an operation of initiating 310 respiratory support by inserting the cannula prongs into the nares of the infant. The method can further include an operation of continuously monitoring 312 the flow rate of gas through the limited-leak cannula.

In some embodiments, the calibration procedure can include measuring the flow rate at a plurality of different set pressures with the prongs freely exposed to generate a calibration curve. As an example, the flow rate could be measured at pressures ranging between 5 and 20 cm $H_2O$ at intervals of 1 or 2 cm $H_2O$. In some embodiments, a curve-fitting algorithm can be applied in order to generate an equation which describes the observed calibration curve. Many different types of linear and non-linear curve-fitting algorithms can be used. In this way, regardless of how the set pressure is changed, the expected maximum flow rate can be estimated.

In some embodiments, the method can further include an operation of choosing automatic or manual re-calibration of parameters if there is a change in the set pressure. In some embodiments, the method can further include using a calibration curve to readjust parameters based on the expected maximum flow rate corresponding to a new set pressure. The term maximum flow rate refers to the flow rate of gas through the cannula at a given set pressure with the prongs freely exposed. By way of non-limiting example, certain parameter values can be changed in proportion to the estimated maximum flow rate. For example, if the maximum flow rate is estimated to change to a higher level due to an increase in pressure setting, then individual parameters (such as the upper or lower bounds of flow rate ranges or other alarm limits) can be automatically changed to correspond to previously specified percentages above zero and below the new maximum flow rate. As another example, if the estimated maximum flow rate changes, individual parameters (such as the upper bound of the flow rate range or other alarm limits) can be automatically changed to correspond to a flow rate at a previously specified absolute difference below the estimated new maximum flow rate (the lower bound would not need to be changed).

In some embodiments, the method can further include re-initiating the calibration procedure if the set pressure changes after initiating respiratory support. In some embodiments, the method can further include displaying instructions on a screen for a re-calibration procedure. In some embodiments, the calibration procedure can be interrupted automatically after detection that the prongs are not freely exposed using various methods of comparing expected flow rates and flow patterns with actual measured flow rates and flow patterns, then issuing a warning of the inappropriate condition for calibration. In some embodiments, the operational parameters can further include a parameter selected from the group consisting of dislodgement parameters, obstruction parameters, and inspiratory breath trigger parameters. Inspiratory breath trigger parameters can include, but are not limited to, absolute flow rate change triggers, flow rate slope triggers, flow rate percentage change from baseline end-expiratory pressure, and the like. In some embodiments, the dislodgement parameters selected from the group consisting of a flow rate threshold and a duration threshold. In some embodiments, the obstruction parameters selected from the group consisting of a flow rate threshold and a duration threshold. In some embodiments, the method can further include determining whether the fit of the limited-leak cannula is optimal for the patient by evaluating the measured flow rate of gas with the nasal prongs in the nares of the infant. For example, in some embodiments, the flow rate of gas can be evaluated to determine whether it is between 20% and 80% of the maximum flow rate. In some embodiments, the operations mode on the ventilator that is specific for unidirectional flow limited-leak cannula use can be selected from the group consisting of NCPAP-LLC (nasal continuous positive airway pressure for limited-leak cannula), NIMV-LLC (nasal intermittent mandatory ventilation for limited-leak cannula), and NSIMV-LLC (nasal synchronized intermittent mandatory ventilation for limited-leak cannula) modes.

Figure 4:
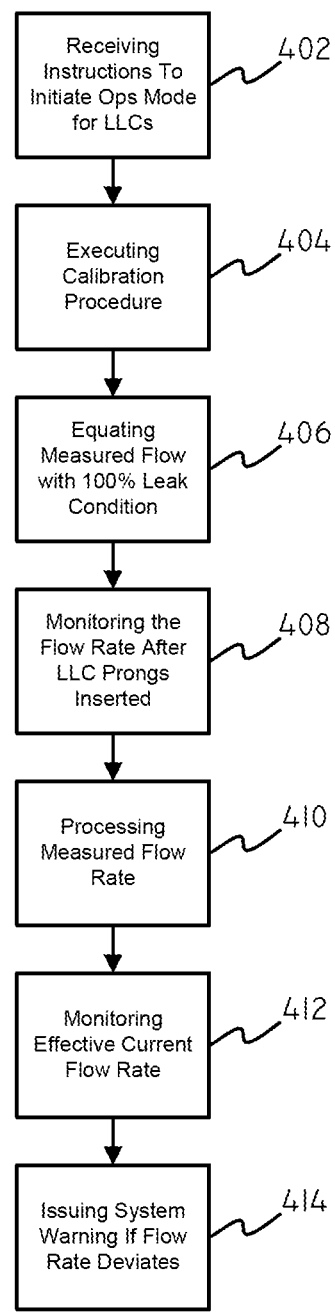
FIG. 4 is a flow chart of operations in accordance with various embodiments herein.

Referring now to FIG. 4, a flow chart of operations in accordance with various embodiments herein is shown. In an embodiment, the method can be a method of controlling ventilator operations. The method can include an operation of receiving instructions from a system user to initiate an operations mode specific for limit-leak cannulas. The method can include an operation of executing a calibration procedure, such as described above.

The method can include an operation of equating the measured flow rate at the set pressure with a 100% leak condition for purposes of calculating leak percentage. The method can include an operation of monitoring the measured flow rate after the prongs of the limited-leak cannula are inserted into the nares of an infant.

In some embodiments, during the calibration procedure, the system collects flow rate data continuously until it meets a statistically acceptable level of consistency, then proceeds with automated setup of parameters as applicable to the selected mode of operation specific for LLC use. In some embodiments, the system uses the detected maximum flow rate, then calculates and stores a maximum and a minimum flow rate (NCPAP mode). In some embodiments, the system detects flow rates at two pressures, then calculates and stores two maxima and two minima of flow rates, corresponding to positive end-expiratory pressure (PEEP) and peak inspiratory pressure (PIP) (NIMV and NSIMV modes).

The method can include an operation of processing the measured flow rate while the prongs are in the patient's nares to correct for artifactual changes to determine an effective current flow rate. By way of example, the method can include calculating a short term average (or moving average) of measured flow rates in order to account for artifactual changes that are not indicative of the true status of the respiratory support. Artifactual changes can also be removed from calculation of the effective current flow rate by dropping outliers, or using digital signal processing techniques, slew rate filtering, band pass filtering, low pass filtering, high pass filtering, sampling parameters, or combinations thereof.

The method can include an operation of monitoring the effective current flow rate to detect flow rates that deviate from a predetermined target flow rate range. In some embodiments, the method can include an operation of issuing a system warning if the effective current flow rate deviates from the predetermined target flow rate range. In some embodiments, the system warning can include displaying a notification on a display screen or touch screen. In some embodiments, the system warning can include an audible alarm. In some embodiments, the system warning can include a message sent over a data network. In some embodiments, the system warning can include combinations of these approaches.

In some embodiments, the calibration procedure can include measuring the flow rate at a plurality of different set pressures to generate a calibration curve. In some embodiments, the method can further include an operation of choosing automatic or manual re-calibration of parameters if there is a change in the set pressure. In some embodiments, the method can further include using the calibration curve to readjust all calibration parameters based on the expected maximum flow rate corresponding to a new set pressure.

In some embodiments, the method further includes re-executing the calibration procedure if the set pressure changes after the prongs of the limited-leak cannula are inserted into the nares of the infant. In some embodiments, the method further includes receiving instructions from a system user regarding operational parameters, the operational parameters including a parameter selected from the group consisting of a desired flow rate range, dislodgement parameters, obstruction parameters, and inspiratory breath trigger parameters. In some embodiments, the dislodgement parameters can be selected from the group consisting of a flow rate threshold and a duration threshold. In some embodiments, the obstruction parameters can be selected from the group consisting of a flow rate threshold and a duration threshold. In some embodiments, the method further includes determining whether the fit of the limited-leak cannula is optimal for the patient. For example, determining whether the fit is optimal can include evaluating the measured flow rate of gas and determining whether it is between 20% and 80% of the maximum flow rate. In some embodiments, the method further includes displaying a graph of respiratory data over time. In some embodiments, the respiratory data is selected from the group consisting of an effective current flow rate and set pressure. In some embodiments, the operations mode on the ventilator that is specific for unidirectional flow limited-leak cannula use is selected from NCPAP-LLC, NIMV-LLC, and NSIMV-LLC modes.

In some embodiments, the method further includes calculating an estimated pressure in the anterior nasal airway of the infant using the set pressure and the effective current flow rate.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adapt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications can be made while remaining within the spirit and scope of the invention.

The invention claimed is:

1. A method of providing respiratory support to an infant comprising:
    attaching a limited-leak cannula having prongs to an inspiratory port of a ventilator with a connection tubing;
    selecting an operations mode on the ventilator that is specific for unidirectional flow limited-leak cannula use;
    initiating a calibration procedure with the prongs of the cannula freely exposed to an ambient pressure, wherein the calibration procedure includes measuring a flow rate of gas through the limited-leak cannula at a set pressure, wherein the flow rate is measured with a hot wire anemometer;
    setting monitoring parameters on the ventilator, the monitoring parameters including a range for desired flow rate;
    initiating respiratory support by inserting the cannula prongs into a pair of nares of the infant; and
    continuously monitoring the flow rate of gas through the limited-leak cannula.

2. The method of claim 1, wherein the calibration procedure includes measuring the flow rate at a plurality of different set pressures to generate a calibration curve.

3. The method of claim 1, further comprising automatically interrupting the calibration procedure after detection that the prongs are not freely exposed to ambient pressure by comparing expected flow rates and flow patterns with actual measured flow rates and flow patterns, then issuing a warning of an inappropriate condition for calibration.

4. The method of claim 1, the operational parameters further including a parameter selected from the group consisting of dislodgement parameters, obstruction parameters, and inspiratory breath trigger parameters.

5. The method of claim 4, the dislodgement parameters selected from the group consisting of a flow rate threshold and a duration threshold and the obstruction parameters selected from the group consisting of a flow rate threshold and a duration threshold.

6. The method of claim 1, further comprising determining whether the fit of the limited-leak cannula is optimal for the patient by evaluating a measured flow rate of gas.

7. The method of claim 1, wherein the operations mode on the ventilator that is specific for unidirectional flow limited-leak cannula use is selected from the group consisting of NCPAP-LLC, NIMV-LLC, and NSIMV-LLC modes.

8. A method of controlling ventilator operations comprising:
    receiving instructions from a system user to initiate an operations mode specific for limit-leak cannulas;
    executing a calibration procedure, the calibration procedure including measuring a gas flow rate at a set pressure from a gas source, wherein the ventilator is connected to a limited-leak cannula having prongs during the calibration procedure and the prongs are freely exposed to an ambient air pressure, wherein the gas flow rate is measured using a flow sensor in a conduit in fluid communication with an inspiratory gas port of the ventilator and the limited-leak cannula;
    equating the measured gas flow rate at the set pressure with a 100% leak condition for purposes of calculating leak percentage;
    monitoring the measured gas flow rate after the prongs of the limited-leak cannula are inserted into a pair of nares of an infant;
    processing the measured gas flow rate to correct for artifactual changes to determine an effective current flow rate;
    monitoring the effective current flow rate to detect flow rates that deviate from a predetermined target flow rate range; and
    issuing a system warning if the effective current flow rate deviates from the predetermined target flow rate range.

9. The method of claim 8, further comprising:
    processing the effective current flow rate during spontaneous breathing (CPAP mode) to determine a representative difference between maximum and minimum flow rate; and
    issuing a system warning if the difference in flow rate between inspiration and expiration has decreased below a predetermined threshold as evidence of possible nasal airway obstruction.

10. The method of claim 9, further comprising automatically interrupting the calibration procedure after detection that the prongs are not freely exposed using various methods of comparing expected flow rates and flow patterns with actual measured flow rates and flow patterns, then issuing a warning of an inappropriate condition for calibration.

11. The method of claim 9, further comprising receiving instructions from a system user regarding operational parameters, the operational parameters including a parameter selected from the group consisting of dislodgement parameters, obstruction parameters, and inspiratory breath trigger parameters.

12. The method of claim 11, the dislodgement parameters selected from the group consisting of a flow rate threshold and a duration threshold and the obstruction parameters selected from the group consisting of a flow rate threshold and a duration threshold.

13. The method of claim 9, further comprising displaying a graph of effective current flow rate and set pressure over time.

14. A medical ventilator comprising:
    a control unit comprising
        a microprocessor;
        a memory;
    a control interface in electrical communication with the control unit;
    a gas supply;
    a control valve in fluid communication with the gas supply, the control unit configured to control the control valve; and
    an inspiratory gas orifice in fluid communication with the control valve;
    a pressure sensor in fluid communication with the inspiratory gas orifice; and
    a flow sensor in fluid communication with the inspiratory gas orifice;
    wherein the control unit is configured to receive instructions from the system user through the control interface regarding entering a mode of operation specific to delivering respiratory support to a patient using a limited-leak cannula;

wherein the mode of operation specific to delivering respiratory support includes execution of a calibration operation including measuring a flow rate of gas through a conduit in fluid communication with the inspiratory gas orifice while a limited-leak cannula is operatively connected to the inspiratory gas orifice and prongs of the limited-leak cannula are freely exposed to ambient gas pressure;

wherein the mode of operation specific to delivering respiratory support further includes monitoring the measured flow rate of gas after the prongs of the limited-leak cannula are positioned to allow gas to flow into the nares of an infant and processing the measured flow rate to correct for artifactual changes to determine an effective current flow rate; and wherein the mode of operation specific to delivering respiratory support further includes monitoring the effective current flow rate to detect flow rates that deviate from a predetermined target flow rate range and issuing a system warning if the effective current flow rate deviates from the predetermined target flow rate range.

15. The medical ventilator of claim 14, further configured to compare the effective current flow rate to an estimated minute ventilation of an infant or an estimated peak flow rate during inspiration.

16. The medical ventilator of claim 14, further configured to issue a system warning if the effective current flow rate is less than an estimated minute ventilation of the infant or an estimated peak flow rate during inspiration.

17. The medical ventilator of claim 14, further configured to determine whether a fit of the limited-leak cannula is optimal for the patient by evaluating the measured flow rate of gas.

* * * * *